United States Patent
Minoguchi et al.

(10) Patent No.: US 8,216,202 B2
(45) Date of Patent: Jul. 10, 2012

(54) TAMPON HAVING AN ASYMMETRIC INSERTION END

(75) Inventors: Ryo Minoguchi, Cincinnati, OH (US);
Ricky Alan Pollard, Moscow, OH (US);
Margaret Henderson Hasse, Wyoming, OH (US); Letha Margie Hines, Cincinnati, OH (US); Diana Lynn Gann, Lebanon, OH (US); Thomas Ward Osborn, III, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 802 days.

(21) Appl. No.: 11/526,041

(22) Filed: Sep. 22, 2006

(65) Prior Publication Data

US 2008/0077109 A1   Mar. 27, 2008

(51) Int. Cl.
*A61F 13/20* (2006.01)

(52) U.S. Cl. ............ 604/385.17; 604/385.18; 604/904; 604/11

(58) Field of Classification Search .......... 604/904, 604/385.17, 385.18, 11–18
See application file for complete search history.

(56) References Cited

U.S. PATENT DOCUMENTS

| | | | |
|---|---|---|---|
| 2,351,836 A | 6/1944 | Popper | |
| 3,738,364 A | 6/1973 | Brien et al. | |
| 3,863,636 A | 2/1975 | Johnson | |
| 3,983,868 A | 10/1976 | Ring | |
| 5,370,633 A | 12/1994 | Villalta | |
| 5,542,914 A | 8/1996 | Van Iten | |
| 5,891,123 A | 4/1999 | Balzar | |
| 5,911,712 A | 6/1999 | Leutwyler et al. | |
| 6,283,952 B1 | 9/2001 | Child et al. | |
| 6,840,927 B2 | 1/2005 | Hasse et al. | |
| 6,932,805 B2 | 8/2005 | Kollwitz et al. | |
| 6,953,456 B2 | 10/2005 | Fuchs et al. | |
| 2004/0049167 A1 | 3/2004 | Hasse et al. | |
| 2004/0199137 A1 * | 10/2004 | Lamb | 604/385.18 |

FOREIGN PATENT DOCUMENTS

| | | |
|---|---|---|
| GB | 2 227 666 | 8/1990 |
| JP | 2003-180741 | 7/2003 |
| WO | WO 2005/058219 | 6/2005 |

OTHER PUBLICATIONS

PCT International Search Report dated Jul. 21, 2008.

\* cited by examiner

*Primary Examiner* — Jacqueline F. Stephens

(74) *Attorney, Agent, or Firm* — Andrew J. Hagerty; Amanda T. Barry

(57) ABSTRACT

Tampons comprising an asymmetric insertion end are provided. The tampon can comprise a substantially symmetrical absorbent mass having an insertion end and a withdrawal end, wherein the insertion end is asymmetric around an X axis of the tampon. A method of improving placement of a tampon in a vagina of a female is also provided.

19 Claims, 15 Drawing Sheets

TAMPON HAVING AN ASYMMETRIC INSERTION END

FIELD OF THE INVENTION

The invention relates to absorbent tampons and more particularly to tampons including an asymmetric insertion end.

BACKGROUND OF THE INVENTION

Catamenial tampons are typically inserted into a vagina of a woman to absorb menstrual discharges during menstruation. It is desirable that a tampon provide leakage protection, that is, the tampon should prevent menstrual discharges from leaking out of the body, for example, onto an undergarment, when the tampon is in use.

In order to facilitate selection of the proper tampon for optimum leakage protection, tampons are categorized by absorbency. Absorbency is generally regulated and publicized so that women can select a tampon with appropriate absorbency corresponding to their expected menstrual flow level. Women often experience unexpected leakage, however, even though they believe they have chosen the correct tampon. In some cases, the unexpected leakage can be classified as "early failure" of the tampon because it occurs before the absorbency of the tampon is fully utilized. Such leakage is undesirable because it results in unpredictable protection along with anxiety about leakage.

It is believed that early failure can be primarily associated with ineffective interception of the menstrual discharge, such as, for example, when the tampon is misplaced within the vagina. The vagina is composed of a highly deformable soft tissue that ends at the cervix, which is composed of stiff, muscular tissue. Currently available tampons have a symmetrically formed insertion end. The stiff cervix in the center of the vagina can deflect such a tampon to the sides of the vagina, which can deform to provide a space for the tampon more easily than the area near the cervix. When a tampon is deflected to the side of the vagina, at least a portion of the tampon may be no longer available in the flow path of the menstrual discharge from the cervix. Thus, some of the menstrual discharge can bypass the tampon and leakage can occur.

In addition, the deflection of the tampon during insertion of the tampon into the vagina can cause the user to feel resistance or push-back during the insertion and can cause discomfort to the user and a lack of confidence in insertion.

As such, it would be desirable to provide a more reliable tampon that provides increased leakage protection. It would also be desirable to provide a tampon that provides improved comfort and confidence during insertion.

SUMMARY OF THE INVENTION

This invention is directed to a tampon comprising an asymmetric insertion end. In certain embodiments, the tampon comprises a substantially symmetrical absorbent mass having an insertion end and a withdrawal end. The insertion end can be asymmetric around an X axis of the tampon. A method of improving placement of a tampon in a vagina of a female is also provided.

DETAILED DESCRIPTION OF THE INVENTION

Figure 1:
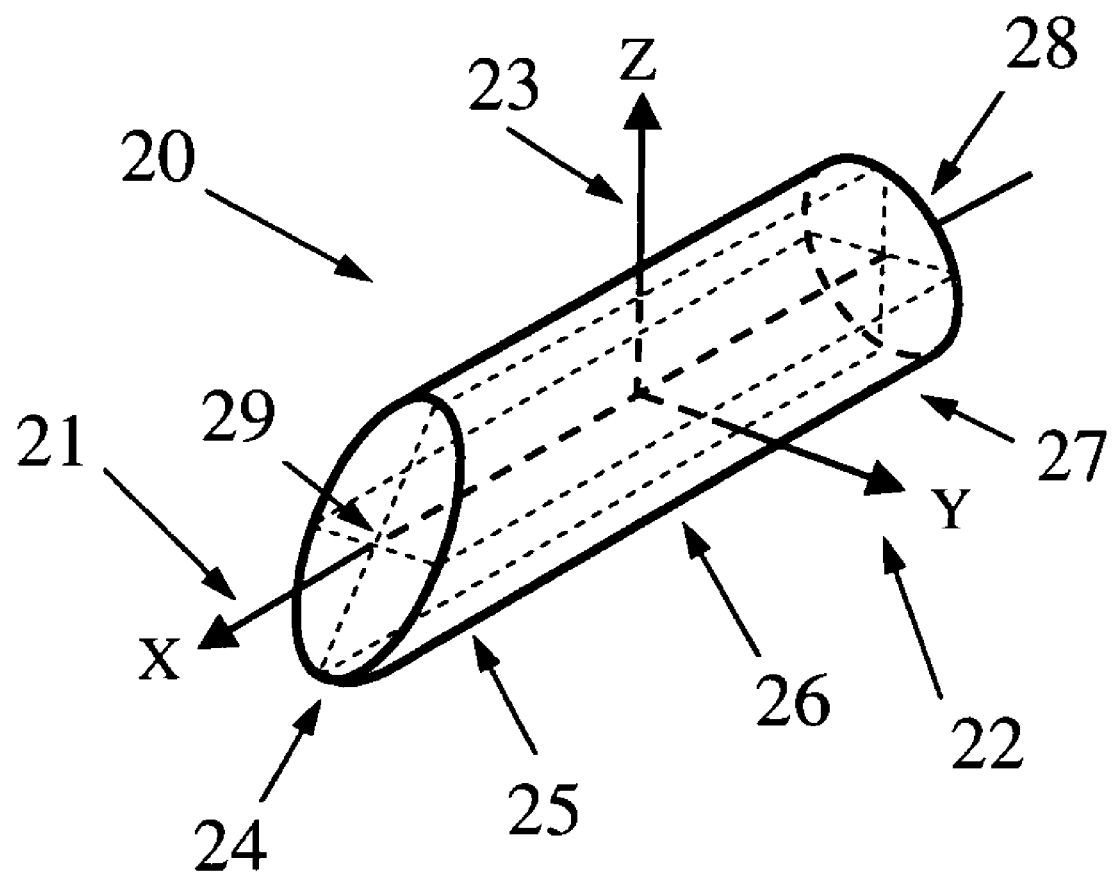
FIG. 1 is a perspective view of the outer surface of a tampon comprising an asymmetric insertion end.

The present invention relates to tampons that include an asymmetric insertion end. Such a tampon design can reduce the deflection of the tampon during insertion, improve placement of the tampon relative to the flow path of the menstrual discharges (i.e., more centered placement of the tampon within the vagina), and/or provide improved interception of the menstrual discharge by the tampon. By reducing deflection of the tampon, early failure leakage can be reduced. Insertion comfort can also be improved by reducing a feeling of resistance or push-back during insertion of the tampon.

As used herein, the term "tampon" refers to any type of absorbent structure such as, e.g., an absorbent mass, that can be inserted into the vaginal canal or other body cavity, such as, e.g., for the absorption of fluid therefrom, to aid in wound healing, and/or for the delivery of materials, such as moisture or active materials such as medicaments. In general, the term "tampon" is used to refer to a finished tampon after the compression and/or shaping process.

As used herein, the term "pledget" refers to an absorbent material prior to the compression and/or shaping of the material into a tampon. Pledgets are sometimes referred to as tampon blanks or softwinds.

As used herein, the term "vaginal canal" refers to the internal genitalia of the human female in the pudendal region of the body. The terms "vaginal canal" or "within the vagina" as used herein are intended to refer to the space located between the introitus of the vagina (sometimes referred to as the sphincter of the vagina) and the cervix.

The term "digital tampon" refers to a tampon that is intended to be inserted into the vaginal canal with the user's finger and generally without the aid of an applicator.

The "total length of the tampon" refers to the length of the tampon beginning at the insertion edge and ending at the withdrawal edge. The total length of the tampon generally does not include the length of any overwrap, secondary absorbent member, or withdrawal cord that extends beyond the main absorbent material ending at the withdrawal edge.

The term "insertion edge" refers to the edge containing the absolute end of the insertion end of the tampon, which is intended to enter the vaginal canal first when inserting the tampon. The phrase "insertion end" refers to the end of the tampon, beginning with the insertion edge.

As used herein, the term "asymmetric insertion end" refers to an insertion end of a tampon that is asymmetric about the X axis.

As used herein, the term "X axis" refers to an axis in a tampon that has a direction generally aligned with a direction of insertion of the tampon and that includes a geometric centroid of the tampon (i.e., a longitudinal "center line" in the tampon).

The "Y axis" and the "Z axis" are axes in a tampon that run perpendicular to the "X axis" and run perpendicular to each other.

As used herein, the term "withdrawal edge" refers to the edge containing the absolute end of the withdrawal end. The phrase "withdrawal end" refers to the end of the tampon opposite the insertion end that begins with the withdrawal edge, and that is intended to exit the vaginal canal first when the tampon is removed from the vagina.

As used herein, the term "center region" refers to the portion of the tampon located between the insertion end and the withdrawal end.

As used herein, the term "tapered" refers to a gradually narrowing portion of a tampon. For example, an insertion end can be "tapered" when the insertion end or a portion thereof has a plurality of gradually decreasing perimeters approaching the insertion edge.

As used herein, "applicator" refers to a device or implement that facilitates the insertion of a tampon into an external orifice of a mammal.

As used herein, the term "superior surface of the vagina" refers to the surface of the vagina that generally faces toward the bladder. The "inferior surface of the vagina" is the surface of the vagina that generally faces toward the bowel.

The tampon of the present invention comprises an asymmetric insertion end, such as, e.g., a tampon that is formed to comprise an asymmetric insertion end. In certain embodiments, the tampon comprises a compressed form that is substantially symmetrical, such as, e.g., substantially cylindrical, and an insertion end that is formed to be asymmetric around the X axis. The tampon can comprise a substantially symmetrical, such as, for example, a substantially cylindrical, center region and withdrawal end, and an insertion end that is asymmetric around the X axis.

An asymmetric insertion end can be any shape suitable for improving placement of the tampon within the vagina as compared to currently available substantially cylindrical tampons, such as, e.g., tampons that have a symmetrically formed insertion end. Suitable shapes of the asymmetric end include, for example, shapes generally similar to the shape of a lipstick tip, a chisel, a pillow, a slot screwdriver, a shovel, a shoehorn, or a beak.

In certain embodiments, a tampon comprising an asymmetric insertion end can reduce the deflection of the tampon around the cervix during insertion and can, for example, make more of the tampon available in the flow path of the menstrual discharges from the cervix. This can provide improved interception of the menstrual discharges and can reduce the likelihood of early failure. A tampon comprising an asymmetric insertion end can provide improved insertion comfort by reducing a feeling of resistance or a push-back during insertion of the tampon.

In certain embodiments, orientation of the insertion end during insertion of the tampon of the present invention can be controlled such that a side of the insertion end, such as, e.g., a side that has a smaller angle to the X axis than any other side of the insertion end, and/or a side comprising a face that is angled, can generally face the superior surface of the vagina. In the case of a digital insertion, controlled orientation can be instructed to the users. The orientation can also or alternatively be achieved by any suitable design of the tampon to facilitate proper orientation of the tampon on the user's finger, such as, e.g., an angled-cut withdrawal end; an asymmetric indentation, recess, and/or pocket in the withdrawal end; an angled cut finger cover; or any other suitable design.

In certain embodiments, the tampon can be inserted with the aid of an applicator that controls orientation of the insertion. When an applicator is employed to aid in control of orientation of the insertion, the controlled orientation can be instructed to the users and/or can be achieved by any suitable design of the applicator. The orientation can also be achieved by any suitable design of the tampon to facilitate proper orientation prior to or after insertion of the tampon within the user's vagina.

FIG. 1 shows one embodiment of the tampon 20 of the present invention. The tampon 20 has an X axis 21. The tampon 20 has a Y axis 22 and a Z axis 23 that are perpendicular to the X axis 21 and are perpendicular to each other. The tampon 20 has an insertion edge 24, an insertion end 25, a center region 26, a withdrawal end 27, and a withdrawal edge 28. As shown in FIG. 1, The insertion end 25 is asymmetric around the X axis 21 of the tampon 20 and is formed in the shape of a lipstick tip. The center region 26 and the withdrawal end 27 can be substantially cylindrical.

Figure 2:
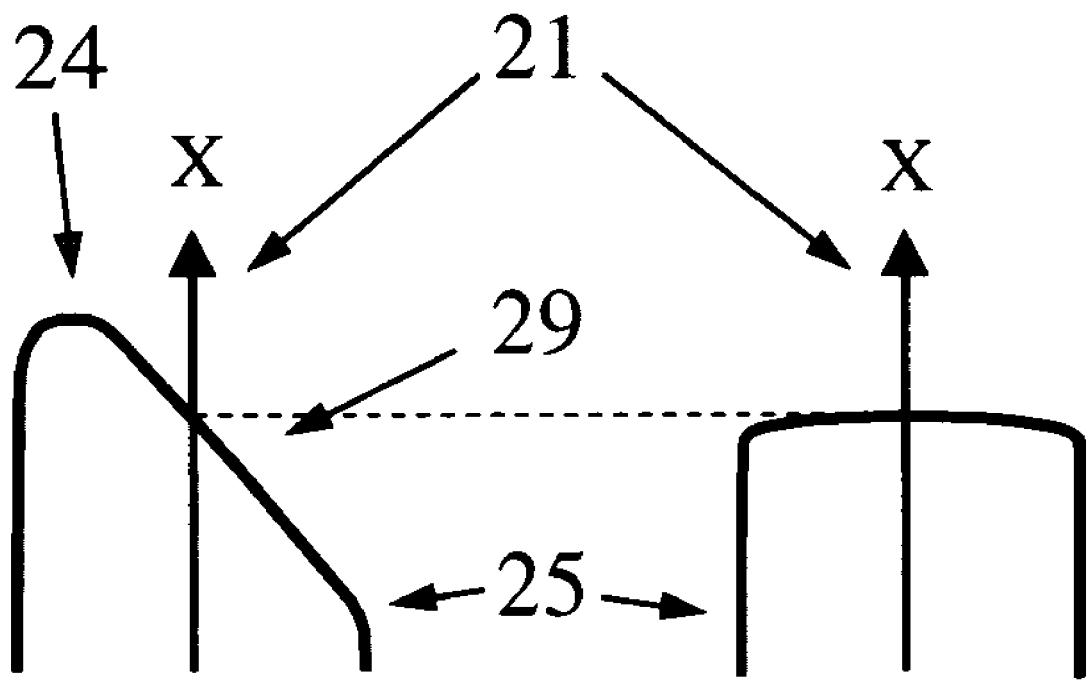
FIG. 2 is a cross-section view of the asymmetric insertion end of the tampon shown in FIG. 1.

FIG. 2 shows cross-sectional views of the asymmetric insertion end 25 of FIG. 1 on the planes that include the X axis 21 and that are perpendicular to the Y axis 22 or the Z axis 23. As shown in FIG. 2, the asymmetric insertion end 25 is substantially asymmetric around the X axis 21 and is formed in the shape of a lipstick tip, such as, e.g., an asymmetric insertion end having a face 29 that is angled to the X axis 21. The edge of the face 29 can be rounded. A cross-section perpendicular to the X axis 21 can be generally semicircular.

Figure 3:
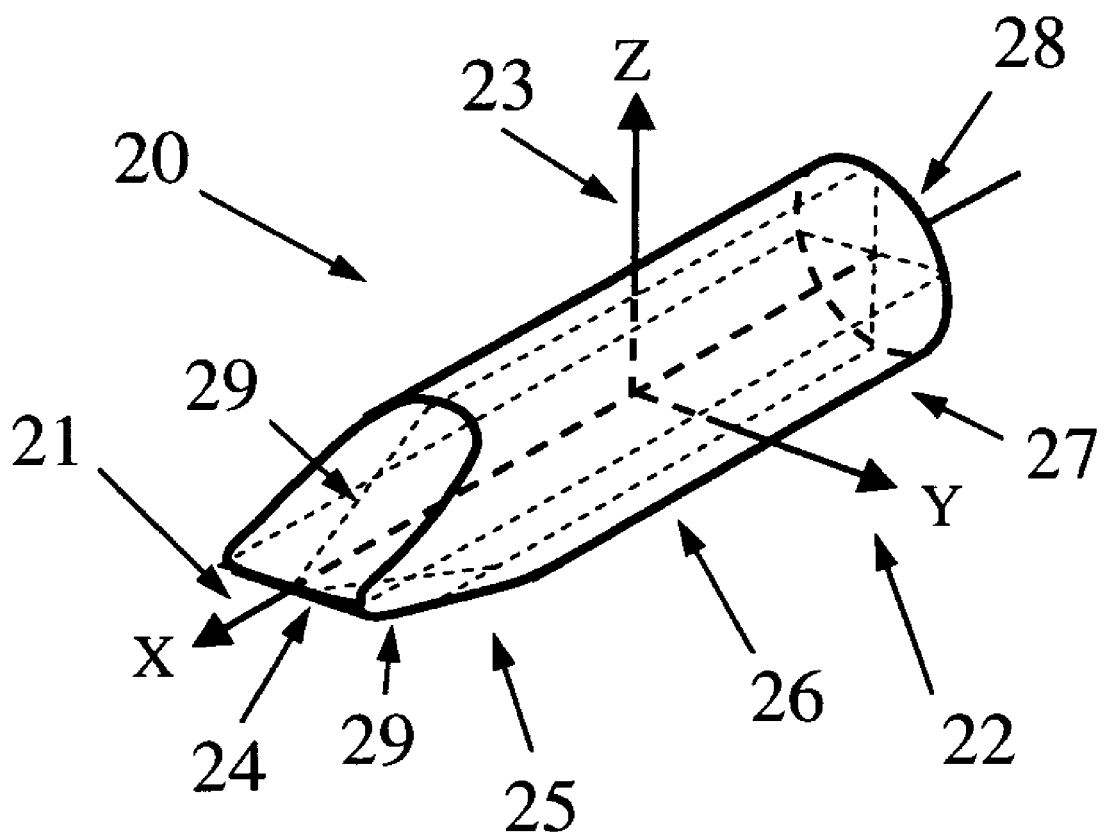
FIG. 3 is a perspective view of the outer surface of a tampon comprising an asymmetric insertion end.

FIG. 3 shows one embodiment of the tampon 20 of the present invention. The tampon 20 has an X axis 21. The tampon 20 has a Y axis 22 and a Z axis 23 that are perpendicular to the X axis 21 and are perpendicular to each other. The tampon 20 has an insertion edge 24, an insertion end 25, a center region 26, a withdrawal end 27, and a withdrawal edge 28. As shown in FIG. 3, the asymmetric insertion end 25 is asymmetric around the X axis 21 of the tampon 20 and is formed in the shape of a chisel. The center region 26 and the withdrawal end 27 can be substantially cylindrical.

Figure 4:
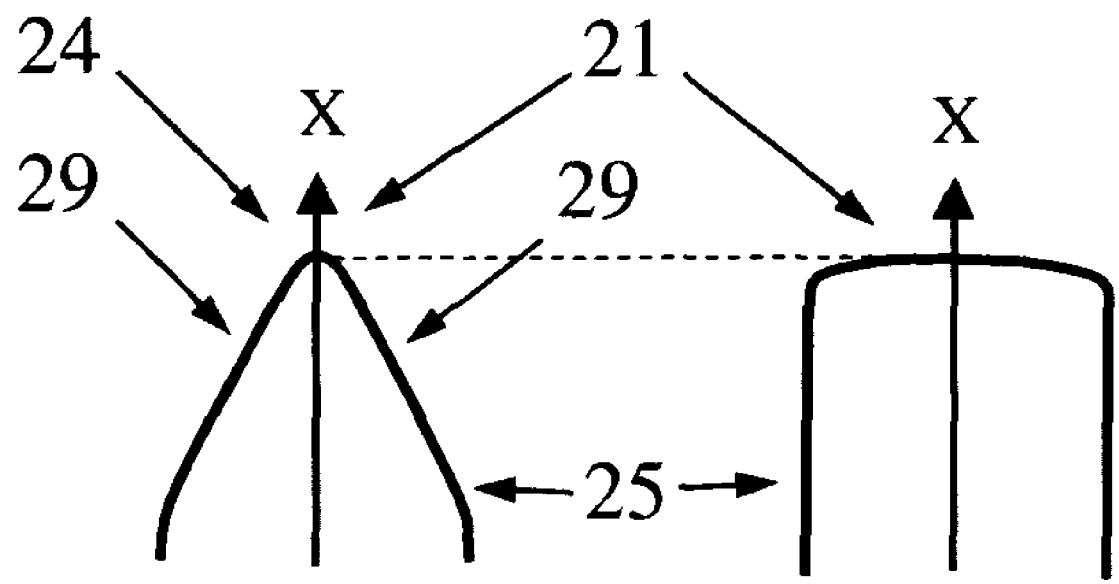
FIG. 4 is a cross-section view of the asymmetric insertion end of the tampon shown in FIG. 3.

FIG. 4 shows cross-sectional views of the asymmetric insertion end 25 of FIG. 3 on the planes that include the X axis 21 and that are perpendicular to the Y axis 22 or the Z axis 23. As shown in FIG. 4, the asymmetric insertion end 25 is substantially asymmetric around the X axis 21 and is formed in the shape of a chisel, such as, e.g., an asymmetric insertion end having two opposing faces 29 that are angled to the X axis 21. The two opposing faces 29 can meet, forming a linear insertion edge 30. In certain embodiments, the edge of the faces 29 can be rounded. A cross-section perpendicular to the X axis 21 can be, for example, generally rectangular to generally racetrack-shaped.

Figure 5:
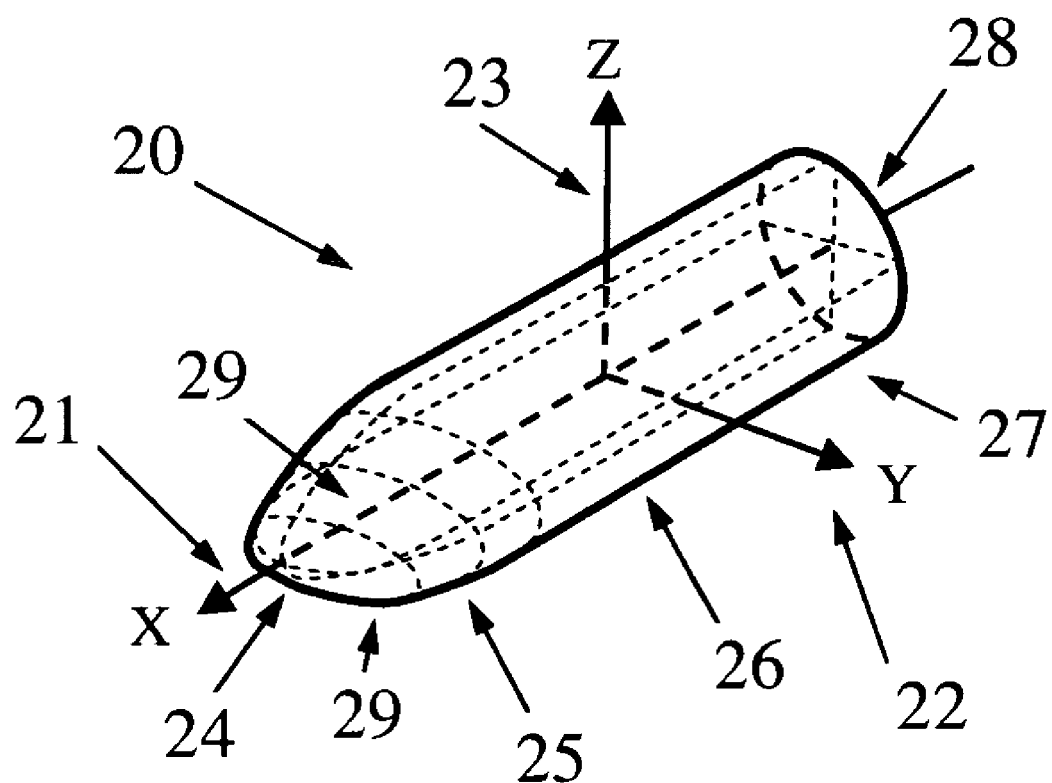
FIG. 5 is a perspective view of the outer surface of a tampon comprising an asymmetric insertion end.

FIG. 5 shows one embodiment of the tampon 20 of the present invention. The tampon 20 has an X axis 21. The tampon 20 has a Y axis 22 and a Z axis 23 that are perpendicular to the X axis 21 and are perpendicular to each other. The tampon 20 has an insertion edge 24, an insertion end 25, a center region 26, a withdrawal end 27, and a withdrawal edge 28. As shown in FIG. 5, the insertion end 25 is asymmetric around the X axis 21 of the tampon 20 and is formed in the shape of a pillow. The center region 26 and the withdrawal end 27 can be substantially cylindrical.

Figure 6:
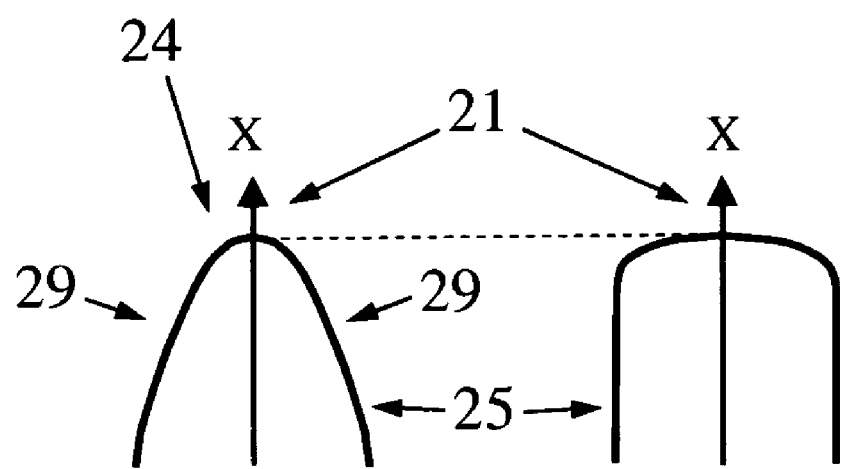
FIG. 6 is a cross-section view of the asymmetric insertion end of the tampon shown in FIG. 5.

FIG. 6 shows cross-sectional views of the asymmetric insertion end 25 of FIG. 5 on the planes that include the X axis 21 and that are perpendicular to the Y axis 22 or the Z axis 23. As shown in FIG. 6, the asymmetric insertion end 25 is substantially asymmetric around the X axis 21 and is formed in the shape of a pillow, such as, e.g., an asymmetric insertion end having one or more faces 29 that form a convex surface that can be gradually tapered and/or flattened toward the insertion edge 24, which can form a curved ridge. The edge of the one or more faces 29 can be rounded. A cross-section perpendicular to the X axis 21 can be generally oval.

Figure 7:
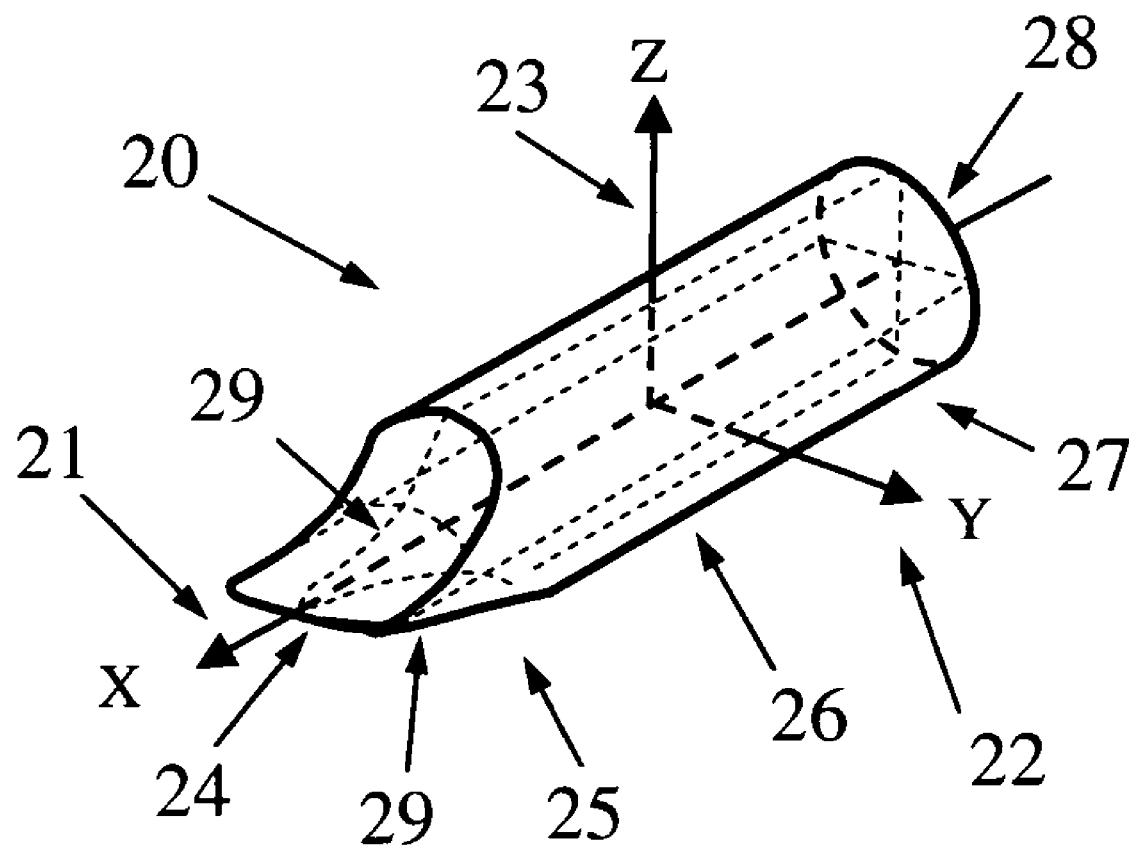
FIG. 7 is a perspective view of the outer surface of a tampon comprising an asymmetric insertion end.

FIG. 7 shows one embodiment of the tampon 20 of the present invention. The tampon 20 has an X axis 21. The tampon 20 has a Y axis 22 and a Z axis 23 that are perpendicular to the X axis 21 and are perpendicular to each other. The tampon 20 has an insertion edge 24, an insertion end 25, a center region 26, a withdrawal end 27, and a withdrawal edge 28. As shown in FIG. 7, the insertion end 25 is asymmetric around the X axis 21 of the tampon 20 and is formed in the shape of a slot screwdriver. The center region 26 and the withdrawal end 27 can be substantially cylindrical.

Figure 8:
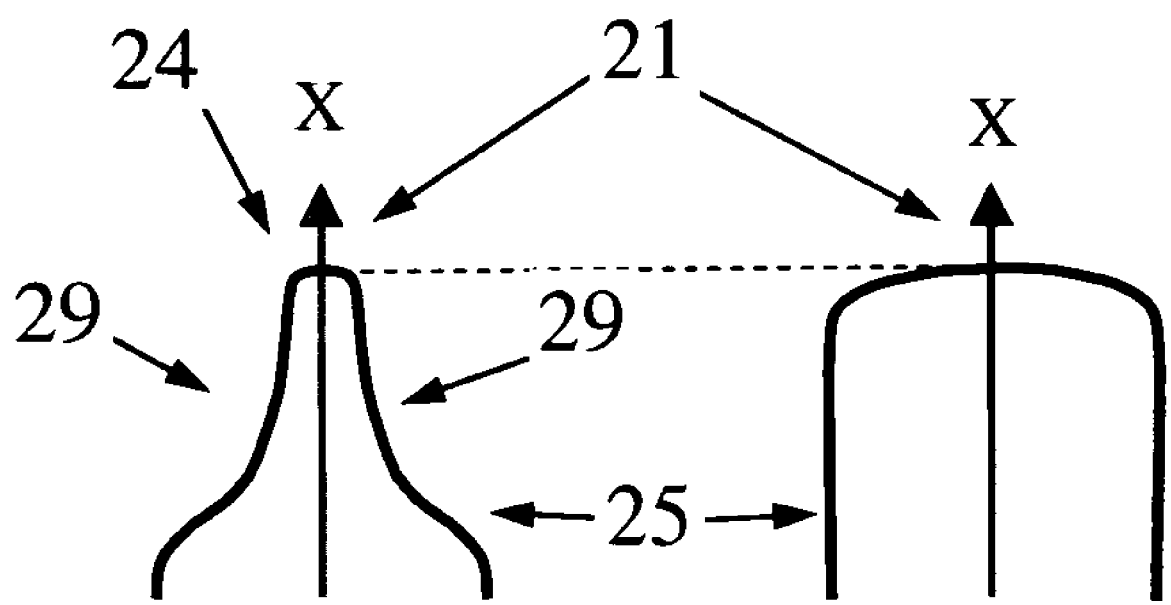
FIG. 8 is a cross-section view of the asymmetric insertion end of the tampon shown in FIG. 7.

FIG. 8 shows cross-sectional views of the asymmetric insertion end 25 of FIG. 7 on the planes that include the X axis 21 and that are perpendicular to the Y axis 22 or the Z axis 23. As shown in FIG. 8, the asymmetric insertion end 25 is substantially asymmetric around the X axis and is formed in the shape of a slot screwdriver such as, e.g., an asymmetric insertion end having two opposing faces 29 that are angled to the X axis 21. The two opposing faces 29 can meet, forming a linear insertion edge 24. The edge of the faces 29 can be tapered to form a protuberance that can be narrow. A cross-section perpendicular to the X axis 21 can be, for example, generally rectangular to generally racetrack-shaped.

Figure 9:
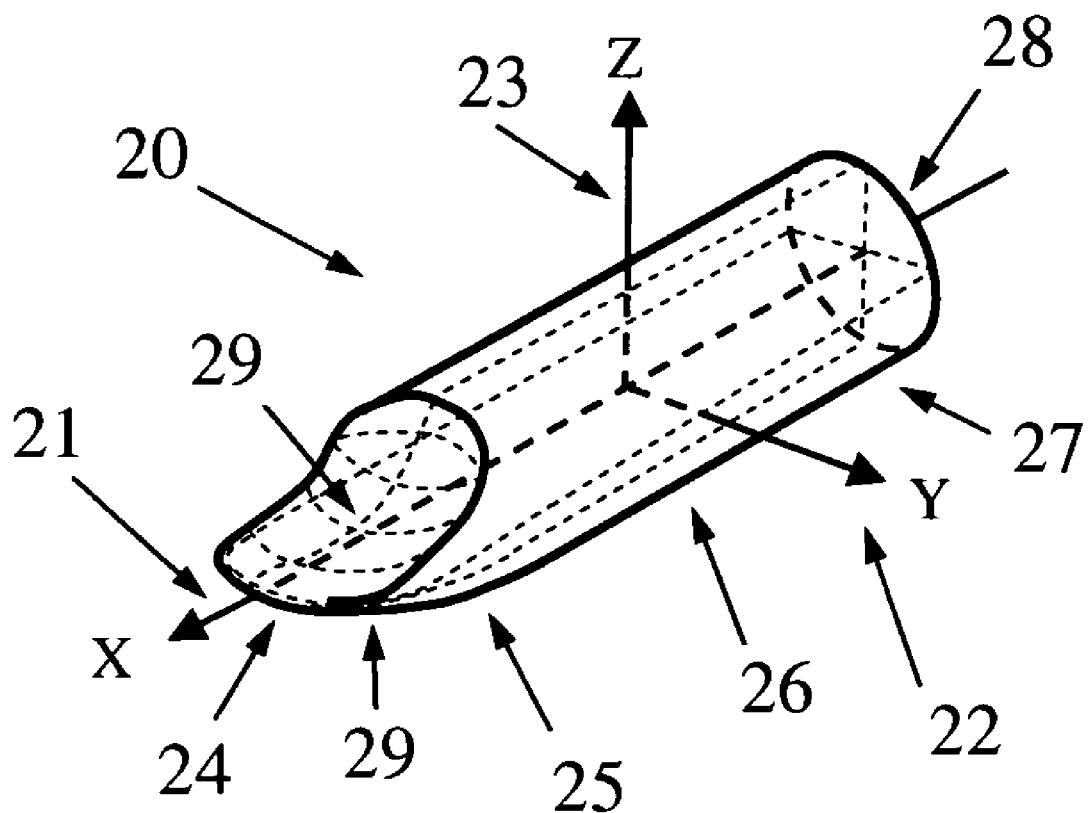
FIG. 9 is a perspective view of the outer surface of a tampon comprising an asymmetric insertion end.

FIG. 9 shows one embodiment of the tampon 20 of the present invention. The tampon 20 has an X axis 21. The tampon 20 has a Y axis 22 and a Z axis 23 that are perpendicular to the X axis 21 and are perpendicular to each other. The tampon 20 has an insertion edge 24, an insertion end 25, a center region 26, a withdrawal end 27, and a withdrawal edge 28. As shown in FIG. 9, the insertion end 25 is asymmetric around the X axis 21 of the tampon 20 and is formed in the shape of a shovel. The center region 26 and the withdrawal end 27 can be substantially cylindrical.

Figure 10:
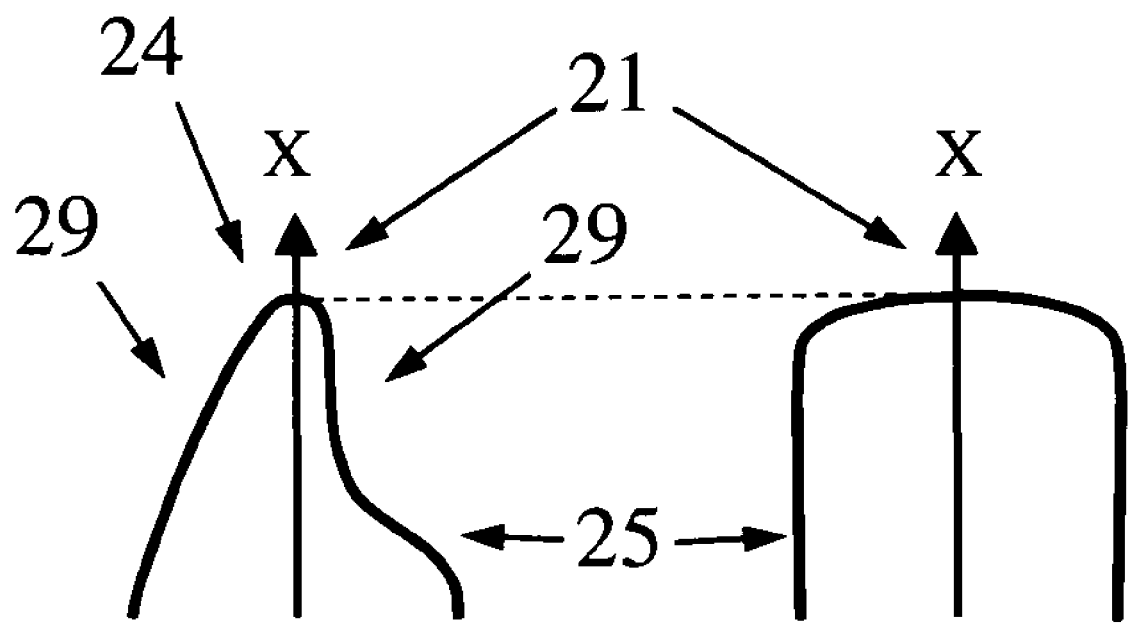
FIG. 10 is a cross-section view of the asymmetric insertion end of the tampon shown in FIG. 9.

FIG. 10 shows cross-sectional views of the asymmetric insertion end 25 of FIG. 9 on the planes that include the X axis 21 and that are perpendicular to the Y axis 22 or the Z axis 23. As shown in FIG. 10, the asymmetric insertion end 25 is substantially asymmetric around the X axis and is formed in the shape of a shovel, such as, e.g., an asymmetric insertion end having two opposing faces 29 that are angled to the X axis 21. The two opposing faces 29 can meet, forming a linear insertion edge 24. One face 29 can be concave and the opposing face 29 can be convex. The edge of the faces 29 can be rounded. A cross-section perpendicular to the X axis 21 can be generally crescentic.

Figure 11:
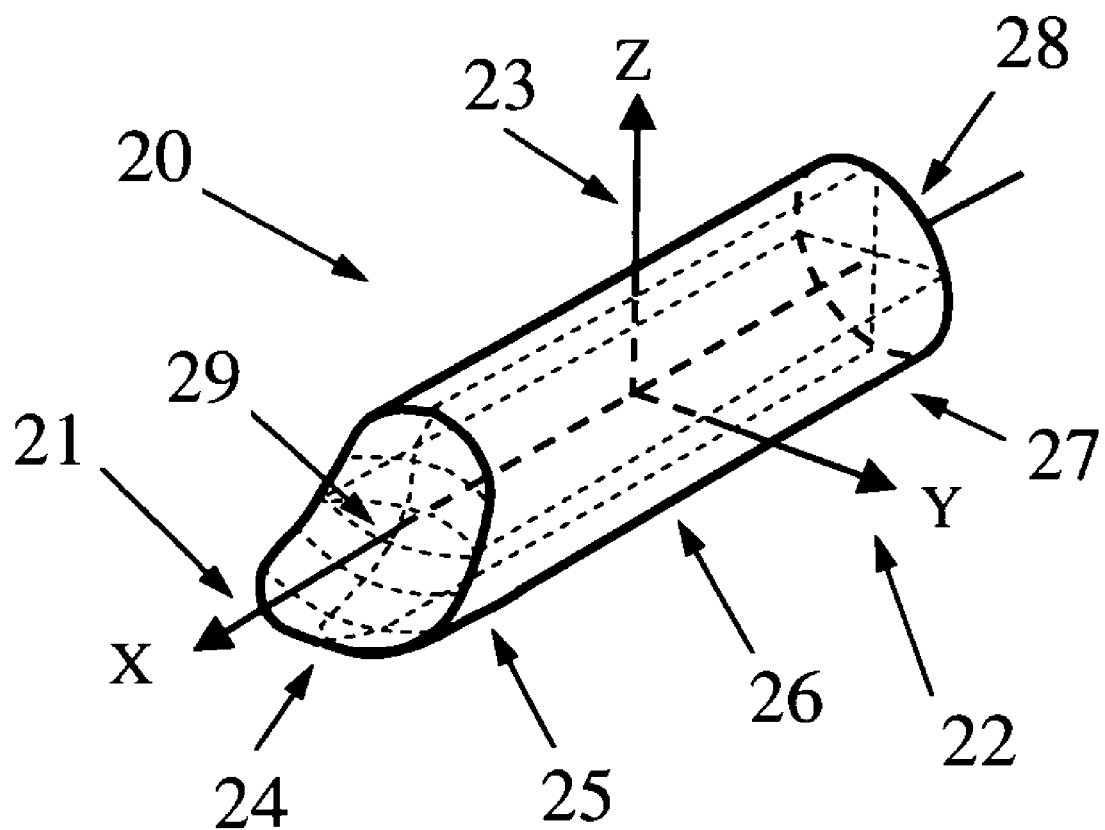
FIG. 11 is a perspective view of the outer surface of a tampon comprising an asymmetric insertion end.

FIG. 11 shows one embodiment of the tampon 20 of the present invention. The tampon 20 has an X axis 21. The tampon 20 has a Y axis 22 and a Z axis 23 that are perpendicular to the X axis 21 and are perpendicular to each other. The tampon 20 has an insertion edge 24, an insertion end 25, a center region 26, a withdrawal end 27, and a withdrawal edge 28. As shown in FIG. 11, the insertion end 25 is asymmetric around the X axis 21 of the tampon 20 and is formed in the shape of a shoehorn. The center region 26 and the withdrawal end 27 can be substantially cylindrical.

Figure 12:
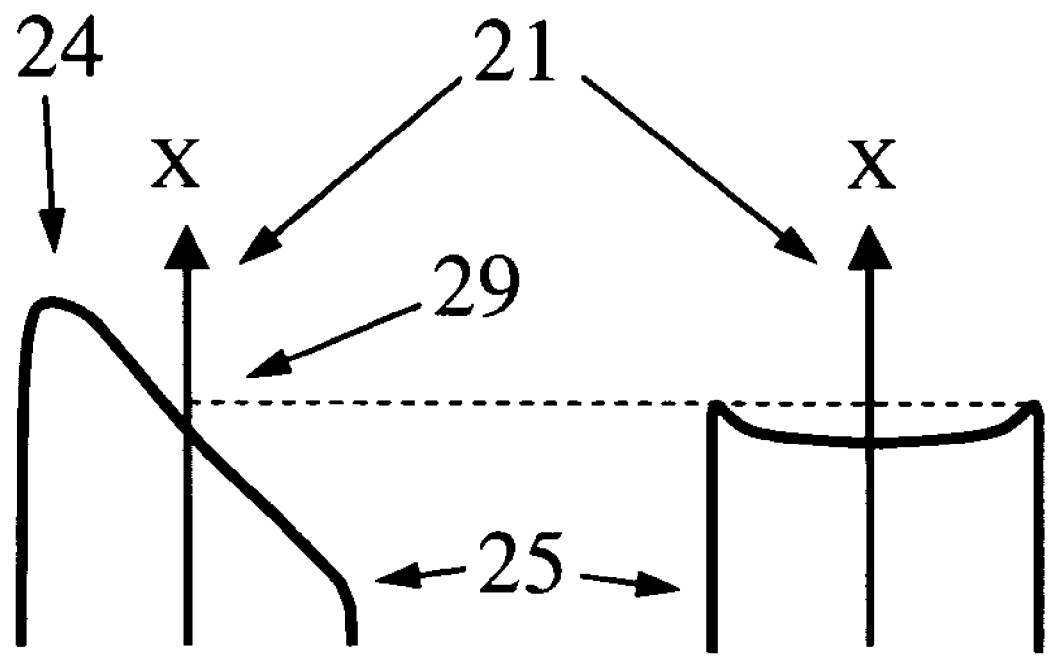
FIG. 12 is a cross-section view of the asymmetric insertion end of the tampon shown in FIG. 11.

FIG. 12 shows cross-sectional views of the asymmetric insertion end 25 of FIG. 11 on the planes that include the X axis 21 and that are perpendicular to the Y axis 22 or the Z axis 23. As shown in FIG. 12, the asymmetric insertion end 25 is substantially asymmetric around the X axis and is formed in the shape of a shoehorn, such as, for example, an asymmetric insertion end having a face 29 that is angled to the X axis 21 and that can be concave. The edge of the face 29 can be rounded. A cross-section perpendicular to the X axis 21 can be generally crescentic.

Figure 13:
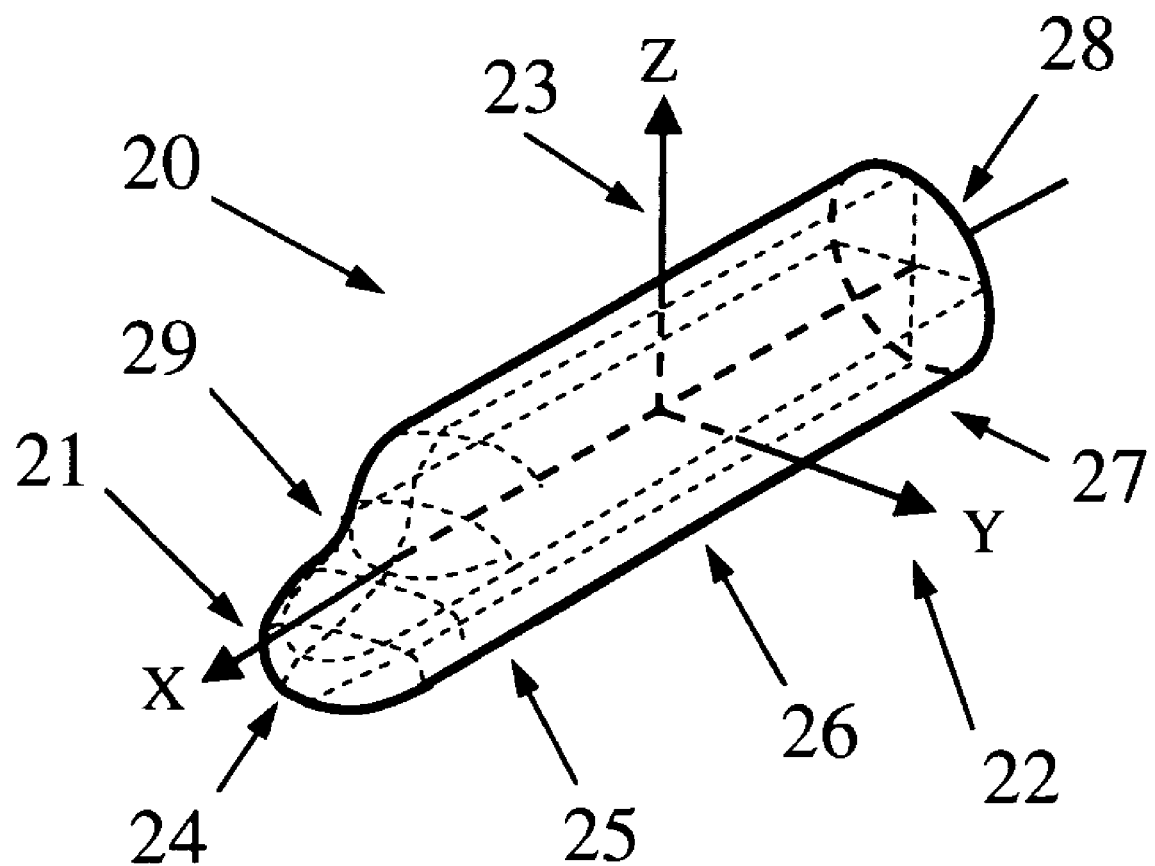
FIG. 13 is a perspective view of the outer surface of a tampon comprising an asymmetric insertion end.

FIG. 13 shows one embodiment of the tampon 20 of the present invention. The tampon 20 has an X axis 21. The tampon 20 has a Y axis 22 and a Z axis 23 that are perpendicular to the X axis 21 and are perpendicular to each other. The tampon 20 has an insertion edge 24, an insertion end 25, a center region 26, a withdrawal end 27, and a withdrawal edge 28. As shown in FIG. 13, the insertion end 25 is asymmetric around the X axis 21 of the tampon 20 and is formed in the shape of a beak. The center region 26 and the withdrawal end 27 can be substantially cylindrical.

Figure 14:
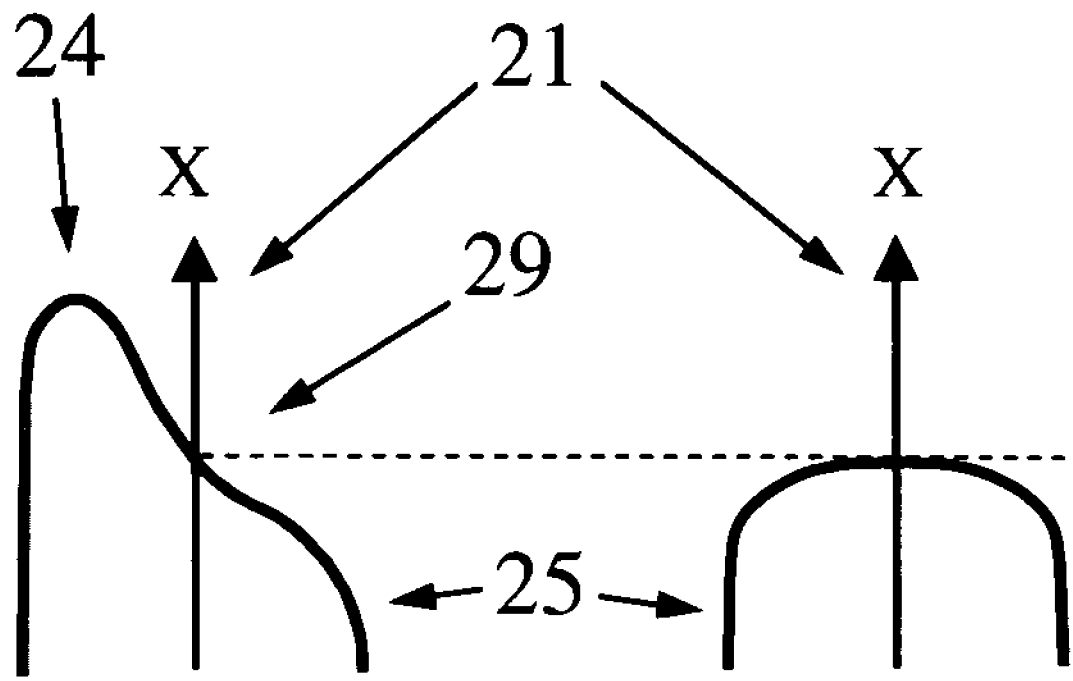
FIG. 14 is a cross-section view of the asymmetric insertion end of the tampon shown in FIG. 13.

FIG. 14 shows cross-sectional views of the asymmetric insertion end 25 of FIG. 13 on the planes that include the X axis 21 and that are perpendicular to the Y axis 22 or the Z axis 23. As shown in FIG. 14, the asymmetric insertion end 25 is substantially asymmetric around the X axis and is formed in the shape of a beak, such as, e.g., an asymmetric insertion end having one or more faces 29 that form a convex surface that can be gradually tapered and/or flattened toward the insertion edge 24, which can form a curved ridge. Part of the surface can be generally flat. The edge of the one or more faces 29 can form a curved ridge. A cross-section perpendicular to the X axis 21 can be generally racetrack-shaped to generally oval to generally hourglass.

The tampon's total length can be measured from the insertion end to the withdrawal end along the X axis. In certain embodiments, a typical tampon for human use can be generally about 10 to about 16 millimeters wide and about 30 to about 60 millimeters long, often depending on absorbency, but can be any suitable width and length. For other mammals, typical tampon dimensions can vary based on differences in their particular vaginal canal geometry.

In certain embodiments, the insertion end can begin at the insertion edge and can end about ⅓ the total length of the tampon along the X axis from the insertion edge. Thus, the total length of the insertion end can be about ⅓ the total length of the tampon. The insertion end can be any suitable length, such as, e.g., about 1/10, about ⅛, about ⅕, about ⅓, or about ½ of the total length of the tampon. As the length of the insertion end varies, the length of the center region and/or withdrawal end can vary accordingly. In certain embodiments, the withdrawal end can begin about ⅔ of the total length of the tampon along the X axis from the insertion edge and can terminate at the withdrawal edge. The withdrawal end can be any suitable length, such as, e.g., about 1/10, about ⅛, about ⅕, about ⅓, or about ½ of the total length of the tampon.

The tampon and any component thereof can comprise a single material or a combination of materials. The materials for the tampon can be formed into a fabric, web, or batt that is suitable for use in the tampon by any suitable process such as, for example, airlaying, carding, wetlaying, hydroentangling, or other known techniques.

The tampon can be formed from a pledget that can be constructed from a wide variety of liquid-absorbing materials suitable for use in absorbent articles. Such materials include, for example, rayon (such as GALAXY rayon (a tri-lobed rayon) or DANUFIL rayon (a round rayon), both available from Kelheim Fibres GmbH of Kelheim, Germany), cotton, folded tissues, woven materials, nonwoven webs, synthetic and/or natural fibers or sheeting, comminuted wood pulp, which is generally referred to as airfelt, foams, or combinations of these materials. Examples of other suitable materials include: creped cellulose wadding; meltblown polymers including coform; chemically stiffened, modified or cross-linked cellulosic fibers; synthetic fibers such as crimped polyester fibers: peat moss; foam; tissue including tissue wraps and tissue laminates: or any equivalent material or combinations of materials, or mixtures of these. Additionally, superabsorbent materials, such as superabsorbent polymers or absorbent gelling materials can be incorporated into the tampon.

The pledget can be any suitable shape, size, material, or construction prior to compression and/or shaping. For example, the pledget can include a rolled, tubed, or flat construction of an absorbent that can be a circle, an oval, a semi-circle, a triangle, a chevron shape, an H shape, a bow-tie shape, or any other suitable shape, such as, e.g., shapes described in, for example, U.S. Pat. Nos. 3,738,364; 5,911,712; 6,740,070; 6.887.266; and 6,953,456.

In certain embodiments, the tampons can be generally "self-sustaining" in that they will generally retain their general shape and size before use. The tampon pledget can be compressed and/or shaped to form a self-sustaining tampon that has a predetermined shape and/or size prior to packaging and/or use, such as, for example, an asymmetric insertion end. In certain embodiments, the self-sustaining tampons typically can be substantially rigid prior to use.

In certain embodiments, the tampon can be formed to have an asymmetric insertion end. For example, the tampon can be compressed or otherwise constructed such that the tampon includes an asymmetric insertion end prior to packaging the tampon, such as, for example, in an applicator and/or a wrapper, and/or prior to purchasing and/or use by a consumer. In certain embodiments, the center region and/or withdrawal end of the tampon can be compressed into a substantially cylindrical configuration, however, other shapes are possible. These can include shapes having a cross section or cross-section element that can be described as rectangular, triangular, trapezoidal, semi-circular, hourglass, or other suitable shapes.

In certain embodiments, the tampon can be a tampon having a radially compressed rolled construction. The tampon can be constructed by rolling and radially compressing a pledget. The pledget can be rolled around a mandrel then compressed with or without the mandrel. In certain embodiments, a cavity left behind after the mandrel is removed can provide a finger pocket. The tampon can also be constructed by pressing a pledget, such as, for example. a cylindrical pledget, in forming dies with a pushrod. A finger pocket can be formed in part of the blank pressed against a convex in the forming dies or the pushrod. The withdrawal cord can be at least partially disposed in the cavity before compression. In certain embodiments, at least a portion of the cord can stick out of the withdrawal end of the finished tampon.

Withdrawal cords useful in the present invention can be made of any suitable material, such as. e.g., cotton and rayon.

In certain embodiments, the withdrawal cord can extend from the withdrawal end and can be at least partially disposed in the finger pocket prior to insertion of the tampon. The withdrawal cord can be at least partially displaced from the finger pocket when the user prepares the tampon for insertion. In certain embodiments, the withdrawal cord can be joined with part of the tampon wrapper so that it can be deployed automatically when at least pail of the wrapper is removed. A joint between the withdrawal cord and the wrapper can have strength such that the joint is maintained during the deployment of the withdrawal cord and breaks off when the withdrawal cord is at least partially extended. In certain embodiments, the joint can be maintained during the deployment of the withdrawal cord and breaks off when the withdrawal cord is fully extended.

The tampon can also or alternatively include one or more overwraps. The overwrap can be any suitable material, such as, for example, rayon. cotton, bicomponent fibers, polyethylene, polypropylene, other suitable natural or synthetic fibers known in the art, and mixtures thereof. In certain embodiments, the tampon can comprise an overwrap material that substantially encloses the compressed tampon.

In certain embodiments, the overwrap can extend from the withdrawal end of the tampon. The excess of the overwrap can be tucked in the finger pocket. The excess overwrap can be pulled out of the finger pocket to provide a finger cover or an absorbent skirt when the user prepares the tampon for insertion. In certain embodiments, the excess of the overwrap can be joined with part of the tampon wrapper so that it can be deployed automatically when the pail of the wrapper is removed. A joint between the excess of the overwrap and the wrapper can have strength such that it is maintained during the deployment and then breaks to separate the overwrap and wrapper once a full spread of the excess of the overwrap is achieved. In certain embodiments, the excess of the overwrap can be joined with the cord and tucked in the finger pocket along with the cord.

The tampon can also or alternatively include a secondary absorbent member, such as, for example, a mass of secondary absorbent material attached to the withdrawal cord proximate the withdrawal end of the tampon. Suitable secondary absorbent members are described in, e.g., U.S. Pat. No. 6,258,075.

In certain embodiments, the tampon can be inserted digitally. When the tampons are intended to be digitally inserted, it can be desirable to provide a finger indent at the withdrawal end of the tampon to aid in insertion, such as. e.g., finger indents described in U.S. Pat. No. 6,283,952. In certain embodiments, the digital tampon can comprise an overwrap material that extends from the withdrawal end and forms a finger cover. The digital tampon can also or alternatively comprise a covering material that extends from the withdrawal end and forms an absorbent skirt.

Alternatively, the tampon can be inserted using an applicator. Any suitable applicator can be used, including, e.g., tube and plunger type arrangements that can be plastic, paper, or other suitable material, and compact type applicators. In certain embodiments, the applicator allows the user to better perceive the shape of the tampon, such as, e.g., an applicator comprising translucent and/or transparent materials, and/or an applicator comprising an insertion end that follows and/or otherwise displays the shape of the enclosed tampon. In certain embodiments, the tampon can be inserted using an applicator wherein the applicator includes an insertion end that is formed to be asymmetric around an X axis of the applicator. The tampon can also be inserted using an applicator that comprises an insertion end that is exposed such that the asymmetric insertion end of the tampon is visible.

In certain embodiments, at least a portion of the asymmetric insertion end of the applicator can be shaped to be similar to the tampon and/or contacts and/or conforms to at least a portion of the surface of the tampon. Rigid insertion end structures can be shaped in a suitable manner, such as, e.g., by injection molding, to provide at least a degree of profiled shape observation. Alternatively, insertion ends of applicators made from flexible or pliable materials, such as films, paper and flexible wovens or non-wovens, can also be used. Such flexible or pliable insertion ends include those which partially or fully enclose the tampon comprising a "sleeve" or a "tube," such as, e.g., in U.S. Pat. Nos. 2,922,422 and 2,922,423; a "sheath," such as, e.g., in U.S. Pat. Nos. 2,092,427 and 3,749,093; a "barrel," such as, e.g., in U.S. Pat. No. 5,135,475; a "bag," such as, e.g., in U.S. Pat. No. 3,358,686; or a "film enclosure," such as, e.g., in U.S. Pat. No. 4,610,659.

The tampons can optionally employ wrappers that conform to the outer surface of the tampon in order to visually show the consumer the tampons packaged therein. Such wrappers are particularly useful when the tampons are intended to be used digitally and/or are not housed in an applicator prior to use. The wrappers can substantially enclose each individual tampon and can be removed prior to insertion and use.

Wrappers can be made in any suitable manner. The wrapper material used can be any material suitable to be used for hygienically wrapping tampons. Suitable wrapper materials include, e.g., polymeric films made of polyethylene, polypropylene, polyester, polystyrene, PET (polyethylenetherephthalate), cellophane, polyamide, poly(vinyl chloride), ethylene-vinyl acetate copolymer and the like; synthetic or natural (e.g. rubber) elastomers; generally occlusive materials such as metallic foils (e.g. aluminum foil); non-occlusive or porous materials. Such as nonwovens, wovens, scrims, meshes and papers; or any other suitable materials. The wrapper can comprise one or more flexible polymeric films, such as, for example, films having a thickness of less than about 1 mm. Wrappers can be made and applied to the tampon using any suitable technique, including, for example, heat-shrinking, heat sealing, adhesives, pressure, stretching, lamination, coating, gluing, embossing, crimping, sewing, stitching, entangling, mechanical interlocking, cold pressure welding, ultrasonic bonding, and/or combinations thereof.

Wrappers can be provided with an opening means comprising at least one line of weakness. This opening means can prevent or reduce separation of the wrapper into more than one piece of wrapper material upon opening of the wrapper. For instance, the line of weakness can only extend around a portion of the wrapped tampon in terms of length and perimeter in order to prevent tearing-off of parts of the wrapper upon opening of the wrapper, which could result in fragmentation of the wrapper.

Tampons of the present invention can be made by any suitable method, such as, e.g., methods known in the art. Suitable methods include, for example, methods that impart heat and/or pressure to the tampon pledget. Such heat and/or pressure cause the fibers to "set" and achieve the compressed form subject to fluid expansion.

A method of improving placement of a tampon in a vagina of a female is also provided. The method includes providing a tampon comprising an insertion end that is asymmetric around an X axis of the tampon, such as, e.g., tampons provided herein, and inserting the tampon into the vagina. The asymmetric insertion end of the tampon can be inserted such that the asymmetric insertion end demonstrates improved placement relative to the flow path of the menstrual discharge from the cervix, such as, for example, increased proximity to the cervix compared to a tampon with a symmetrical insertion end. The improved placement of the insertion end of the tampon can result in an increase in the interception of menstrual fluid from the cervix and/or decreased leakage. In certain embodiments, the tampon can be inserted into the vagina such that a side of the insertion end having a face that is angled relative to the X axis generally faces the superior surface of the vagina.

Figure 15:
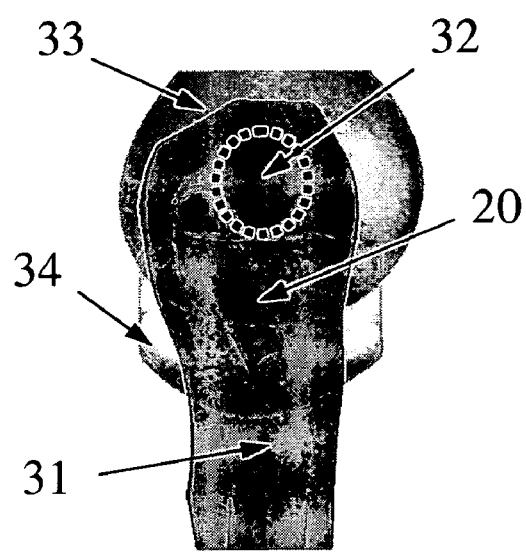
FIG. 15 is a diagram of a computer generated simulation demonstrating deflection of a tampon with a symmetric insertion end.
Figure 16:
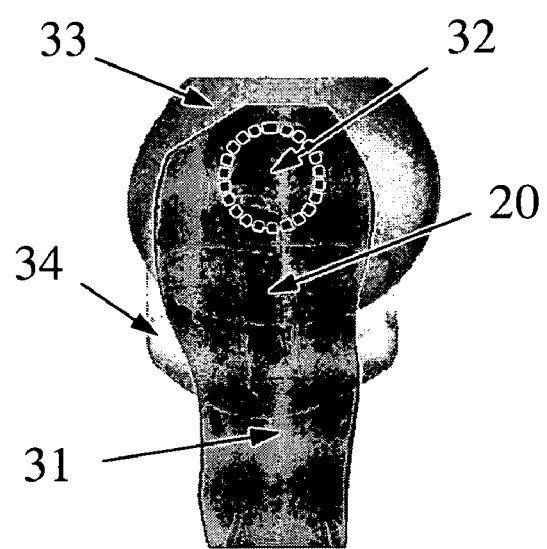
FIG. 16 is a diagram of a computer generated simulation demonstrating improved placement of a tampon with an asymmetric insertion end compared to the tampon shown in FIG. 15.

As shown in FIG. 15, a commercially available tampon 20 with a symmetric insertion end can be deflected to the side of the cervix 32 after insertion into the vagina 31. The deflection can result in decreased interception of menstrual fluid flowing from the cervix 32 and increased leakage outside of the user's body. As shown in FIG. 16, digital insertion of a tampon 20 with an asymmetric insertion end can result in improved placement of the tampon 20 relative to the flow path of the menstrual discharge after insertion into the vagina 31, which can result in improved interception of menstrual fluid and increased insertion comfort. The bladder 34 and uterus 33 are also shown in FIGS. 15 and 16.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A tampon comprising a self-sustaining, compressed cylindrical absorbent mass having an insertion end and a withdrawal end, wherein the insertion end is asymmetric around an X axis of the tampon.

2. A tampon according to claim 1, wherein the insertion end comprises a shape that is generally similar to the shape of a lipstick tip, a chisel, a pillow, a slot screwdriver, a shovel, a shoehorn, or a beak.

3. A tampon according to claim 1, wherein the tampon is a digital tampon.

4. A tampon according to claim 1, wherein the tampon is disposed within an applicator.

5. A tampon according to claim 4, wherein the applicator comprises an insertion end, and wherein the insertion end of the applicator is asymmetric around an X axis of the applicator.

6. A tampon according to claim 4, wherein the applicator comprises an insertion end, and wherein the tampon is exposed at the insertion end of the applicator.

7. A tampon according to claim 1, wherein a side of the insertion end having a smallest angle to the X axis generally faces the superior surface of a vagina when the tampon is inserted into the vagina.

8. A tampon according to claim 1, wherein the tampon comprises a covering material, the absorbent mass being substantially enclosed by the covering material.

9. A tampon according to claim 8, wherein the covering material extends beyond the withdrawal end to form a finger cover.

10. A tampon according to claim 8, wherein the covering material extends beyond the withdrawal end to form an absorbent skirt.

11. A tampon comprising a self-sustaining, compressed absorbent mass having an insertion end, a center region, and a withdrawal end, wherein the center region is cylindrical, and wherein the insertion end is asymmetric around an X axis of the tampon.

12. A tampon according to claim 11, wherein the withdrawal end is cylindrical.

13. A tampon according to claim 11, wherein the insertion end includes one or more faces that are at an angle to the X axis.

14. A tampon according to claim 11, wherein the insertion end is tapered.

15. A method of improving placement of a tampon in a vagina of a female comprising:

providing a tampon comprising a self-sustaining, compressed absorbent mass having an insertion end that is asymmetric around an X axis of the tampon, the tampon further comprising a center region, wherein the center region is cylindrical; and inserting the tampon into the vagina.

16. A method according to claim 15, wherein the vagina comprises a superior surface and an inferior surface, and wherein the tampon is inserted into the vagina such that a side of the insertion end having a face that is angled relative to the X axis generally faces the superior surface.

17. A method according to claim 15, wherein the tampon comprises a withdrawal end, wherein the withdrawal end is cylindrical.

18. A method according to claim 15, wherein the insertion end includes one or more faces that are at an angle to the X axis.

19. A method according to claim 15, wherein the insertion end is tapered.

* * * * *